(12) United States Patent
Kawaura et al.

(10) Patent No.: US 8,979,736 B2
(45) Date of Patent: Mar. 17, 2015

(54) TREATMENT ENDOSCOPE

(75) Inventors: Masayuki Kawaura, Hachioji (JP);
Yoshiaki Ito, Fuchu (JP); Hirokazu Tanaka, Hachioji (JP); Hideya Kitagawa, Hachioji (JP); Hajime Tamura, Sagamihara (JP)

(73) Assignee: Olympus Corporation, Tokyo (JP)

( * ) Notice: Subject to any disclaimer, the term of this patent is extended or adjusted under 35 U.S.C. 154(b) by 405 days.

(21) Appl. No.: 13/236,129

(22) Filed: Sep. 19, 2011

(65) Prior Publication Data

US 2012/0004503 A1  Jan. 5, 2012

Related U.S. Application Data

(63) Continuation of application No. PCT/JP2010/054557, filed on Mar. 17, 2010.

(30) Foreign Application Priority Data

Mar. 19, 2009  (JP) ................................. 2009-068518

(51) Int. Cl.
*A61B 1/00* (2006.01)
*A61M 25/00* (2006.01)
(Continued)

(52) U.S. Cl.
CPC ............. *A61B 1/018* (2013.01); *A61B 1/00087* (2013.01); *A61B 1/00105* (2013.01);
(Continued)

(58) Field of Classification Search
CPC .............. A61B 2019/2242; A61B 2017/00477
USPC ......... 600/104, 109, 146, 101, 160, 139, 153, 600/152, 136, 125, 112, 132, 114; 606/108, 606/46; 128/202.27; 604/164.09, 167.06, 604/528, 523, 533
See application file for complete search history.

(56) References Cited

U.S. PATENT DOCUMENTS 5,178,130 A * 1/1993 Kaiya .......................... 600/109
5,569,157 A  10/1996 Nakazawa et al.
(Continued)

FOREIGN PATENT DOCUMENTS

JP   8-47476 A   2/1996
JP  10-258022 A  9/1998
(Continued)

OTHER PUBLICATIONS

Extended European Search Report (EESR) dated Jun. 18, 2012 (in English) in counterpart European Application No. 10753554.4.
(Continued)

*Primary Examiner* — John P Leubecker
*Assistant Examiner* — Ronald D Colque
(74) *Attorney, Agent, or Firm* — Holtz, Holtz, Goodman & Chick PC

(57) ABSTRACT

A treatment endoscope includes that a body cavity insertion portion which includes a main body distal hard portion, and a main body curving portion provided to a proximal side of the main body distal hard portion, one or more treatment arm/arms projecting to a distal side from the main body distal hard portion, each of the treatment arm/arms including a curving mechanism, an operation portion provided to the proximal side of the body cavity insertion portion, and an observation section configured to image a field of view in a body cavity, the observation section including an imaging section provided within the main body distal hard portion. The treatment endoscope includes that an operation portion attaching/detaching mechanism configured to removably attach the operation portion to the body cavity insertion portion, and an observation section attaching/detaching mechanism configured to removably attach the observation section to the body cavity insertion portion.

8 Claims, 17 Drawing Sheets

(51) Int. Cl.
  *A61M 39/00* (2006.01)
  *A61B 1/018* (2006.01)
  *A61B 17/29* (2006.01)
  *G02B 23/24* (2006.01)
  *A61B 17/00* (2006.01)
  *A61B 19/00* (2006.01)

(52) U.S. Cl.
  CPC .............. *A61B1/00128* (2013.01); *A61B 17/29* (2013.01); *G02B 23/2476* (2013.01); *A61B 2017/00477* (2013.01); *A61B 2017/2906* (2013.01); *A61B 2019/2242* (2013.01)
  USPC ........... 600/104; 600/136; 600/146; 604/523; 604/533

(56) References Cited

U.S. PATENT DOCUMENTS

| | | | |
|---|---|---|---|
| 5,879,288 A * | 3/1999 | Suzuki et al. | 600/176 |
| 5,971,917 A * | 10/1999 | Komi et al. | 600/159 |
| 6,004,263 A * | 12/1999 | Nakaichi et al. | 600/176 |
| 6,013,024 A | 1/2000 | Mitsuda et al. | |
| 6,319,197 B1 * | 11/2001 | Tsuji et al. | 600/132 |
| 6,447,444 B1 | 9/2002 | Avni et al. | |
| 6,569,084 B1 * | 5/2003 | Mizuno et al. | 600/102 |
| 6,994,667 B2 * | 2/2006 | Singh | 600/105 |
| 7,220,227 B2 * | 5/2007 | Sasaki et al. | 600/154 |
| 7,922,650 B2 * | 4/2011 | McWeeney et al. | 600/104 |
| 8,485,965 B2 * | 7/2013 | Ito et al. | 600/112 |
| 8,517,926 B2 * | 8/2013 | Uchimura | 600/152 |
| 8,529,439 B2 * | 9/2013 | Ito et al. | 600/156 |
| 8,608,649 B2 * | 12/2013 | McWeeney et al. | 600/146 |
| 2002/0188174 A1 * | 12/2002 | Aizawa et al. | 600/118 |
| 2003/0018237 A1 * | 1/2003 | Okada | 600/146 |
| 2003/0032860 A1 | 2/2003 | Avni et al. | |
| 2003/0078475 A1 * | 4/2003 | Hirata et al. | 600/152 |
| 2004/0054254 A1 * | 3/2004 | Miyake | 600/104 |
| 2004/0162465 A1 * | 8/2004 | Carrillo | 600/104 |
| 2004/0225187 A1 * | 11/2004 | Kamrava et al. | 600/139 |
| 2005/0004431 A1 * | 1/2005 | Kogasaka et al. | 600/117 |
| 2005/0065399 A1 * | 3/2005 | Sasaki et al. | 600/106 |
| 2005/0149067 A1 * | 7/2005 | Takemoto et al. | 606/144 |
| 2005/0267335 A1 * | 12/2005 | Okada et al. | 600/173 |
| 2005/0272975 A1 * | 12/2005 | McWeeney et al. | 600/113 |
| 2006/0116550 A1 * | 6/2006 | Noguchi et al. | 600/132 |
| 2006/0149129 A1 * | 7/2006 | Watts et al. | 600/113 |
| 2006/0189845 A1 * | 8/2006 | Maahs et al. | 600/146 |
| 2006/0229496 A1 * | 10/2006 | Windheuser et al. | 600/117 |
| 2006/0235304 A1 * | 10/2006 | Harhen et al. | 600/459 |
| 2006/0252993 A1 * | 11/2006 | Freed et al. | 600/146 |
| 2006/0287576 A1 * | 12/2006 | Tsuji et al. | 600/132 |
| 2007/0038028 A1 * | 2/2007 | Uchimura et al. | 600/144 |
| 2007/0167675 A1 * | 7/2007 | Miyamoto et al. | 600/104 |
| 2007/0167676 A1 * | 7/2007 | Miyamoto et al. | 600/104 |
| 2007/0167679 A1 * | 7/2007 | Miyamoto et al. | 600/106 |
| 2007/0167680 A1 * | 7/2007 | Miyamoto et al. | 600/106 |
| 2007/0185385 A1 * | 8/2007 | Noguchi et al. | 600/132 |
| 2007/0191886 A1 * | 8/2007 | Dejima et al. | 606/222 |
| 2007/0197864 A1 * | 8/2007 | Dejima et al. | 600/106 |
| 2007/0198000 A1 * | 8/2007 | Miyamoto et al. | 604/523 |
| 2007/0213702 A1 * | 9/2007 | Kogasaka et al. | 606/32 |
| 2007/0213749 A1 * | 9/2007 | Kogasaka et al. | 606/153 |
| 2007/0219411 A1 * | 9/2007 | Dejima et al. | 600/141 |
| 2007/0238927 A1 * | 10/2007 | Ueno et al. | 600/145 |
| 2007/0249897 A1 * | 10/2007 | Miyamoto et al. | 600/104 |
| 2008/0039693 A1 * | 2/2008 | Karasawa | 600/175 |
| 2008/0051631 A1 * | 2/2008 | Dejima et al. | 600/114 |
| 2008/0188868 A1 * | 8/2008 | Weitzner et al. | 606/130 |
| 2008/0188869 A1 * | 8/2008 | Weitzner et al. | 606/130 |
| 2008/0188871 A1 * | 8/2008 | Smith et al. | 606/139 |
| 2008/0188890 A1 * | 8/2008 | Weitzner et al. | 606/205 |
| 2008/0221391 A1 * | 9/2008 | Weitzner et al. | 600/118 |
| 2008/0243176 A1 * | 10/2008 | Weitzner et al. | 606/206 |
| 2008/0287735 A1 * | 11/2008 | Takemoto et al. | 600/114 |
| 2008/0287737 A1 | 11/2008 | Dejima | |
| 2008/0306339 A1 | 12/2008 | Hashimoto et al. | |
| 2009/0023985 A1 * | 1/2009 | Ewers | 600/104 |
| 2009/0036736 A1 | 2/2009 | Dejima et al. | |
| 2009/0171150 A1 * | 7/2009 | Iede et al. | 600/112 |
| 2009/0287043 A1 * | 11/2009 | Naito et al. | 600/104 |

FOREIGN PATENT DOCUMENTS

| | | |
|---|---|---|
| JP | 2001-521806 A | 11/2001 |
| JP | 2005-95590 A | 4/2005 |
| JP | 2007-236812 A | 9/2007 |
| WO | WO 2004/103430 A2 | 2/2004 |
| WO | WO 2007/080974 A1 | 7/2007 |

OTHER PUBLICATIONS

Japanese Office Action dated Feb. 7, 2012 (and English translation thereof) in counterpart Japanese Application No. 2009-068518.
International Search Report dated Jun. 22, 2010 in counterpart International Application No. PCT/JP2010/054557.
International Preliminary Report on Patentability (IPRP) dated Oct. 27, 2011 (in English) issued in parent International Application No. PCT/JP2010/054557.

* cited by examiner

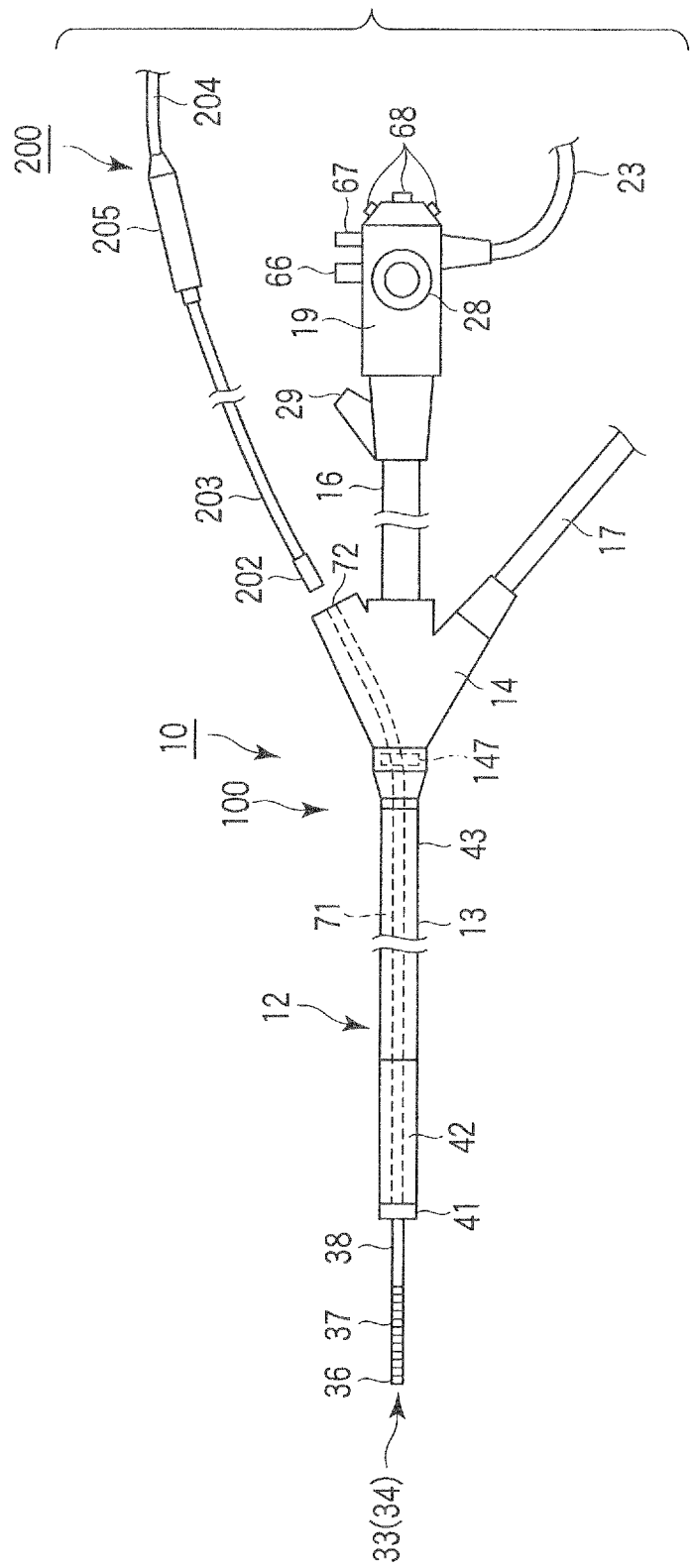
F I G. 2

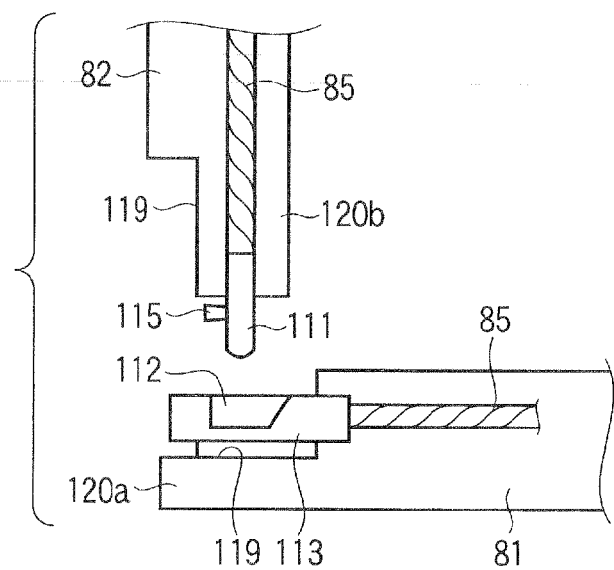
F I G. 14A
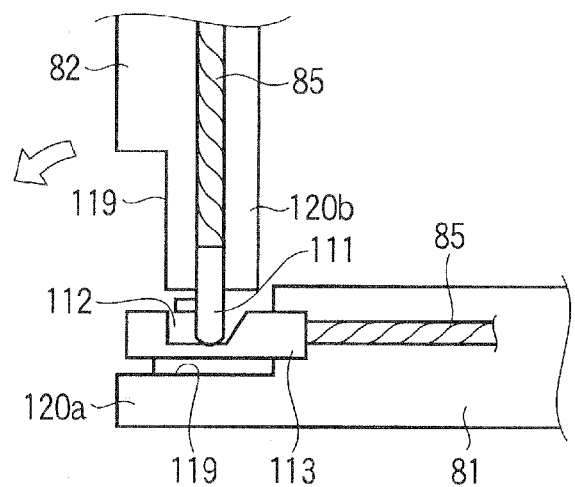
F I G. 14B

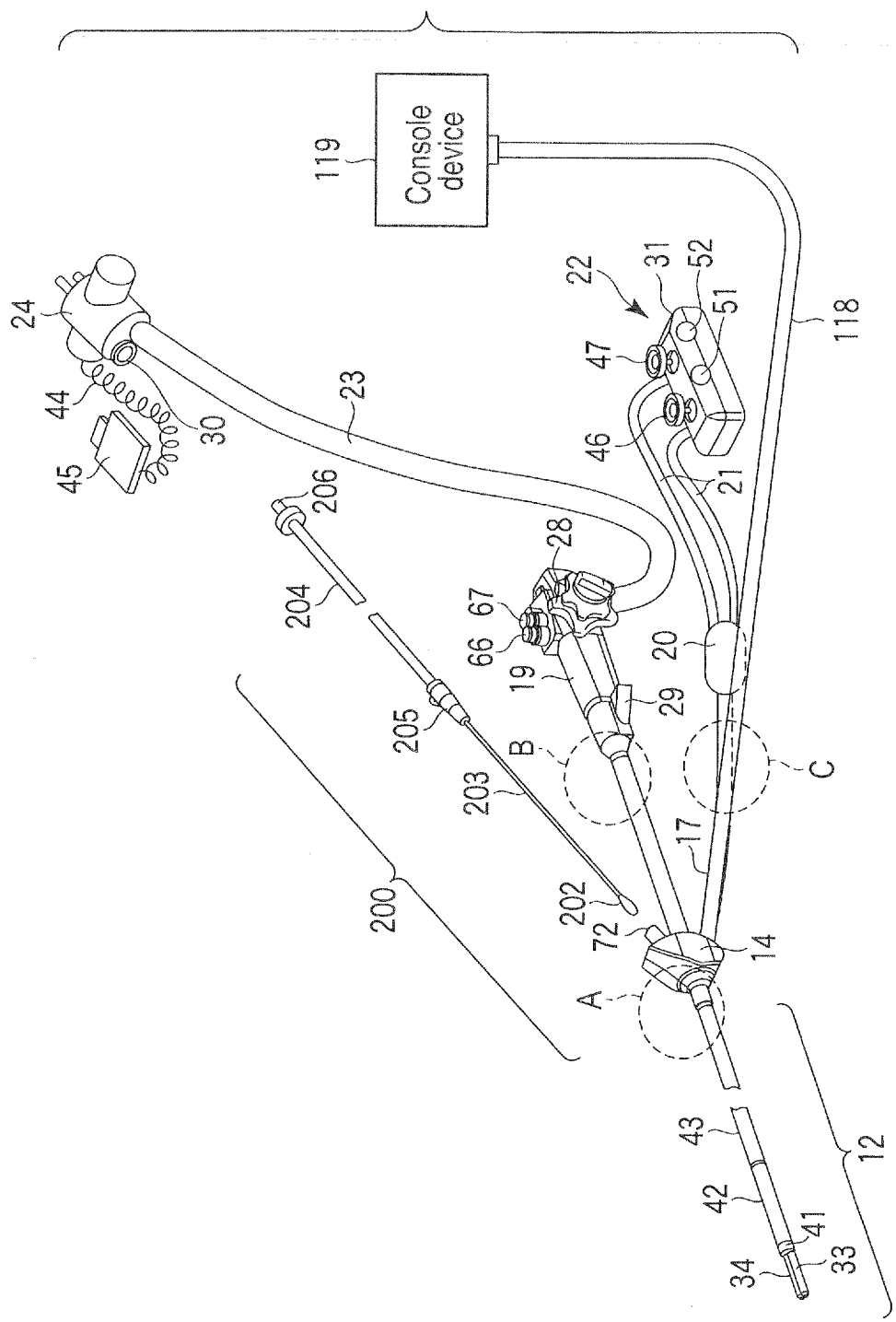
F I G. 18

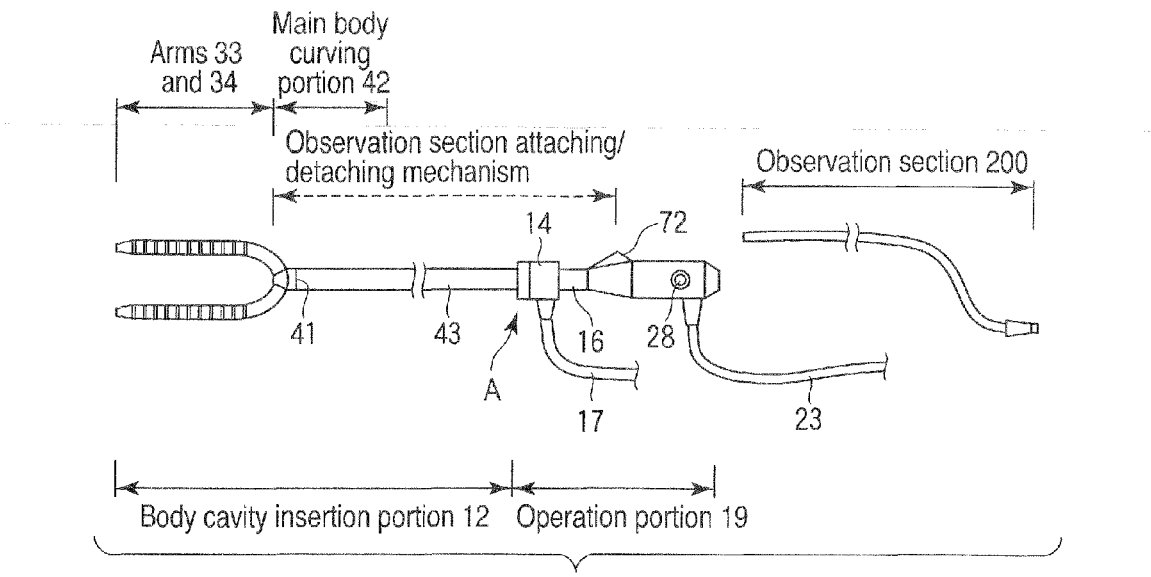
F I G. 19
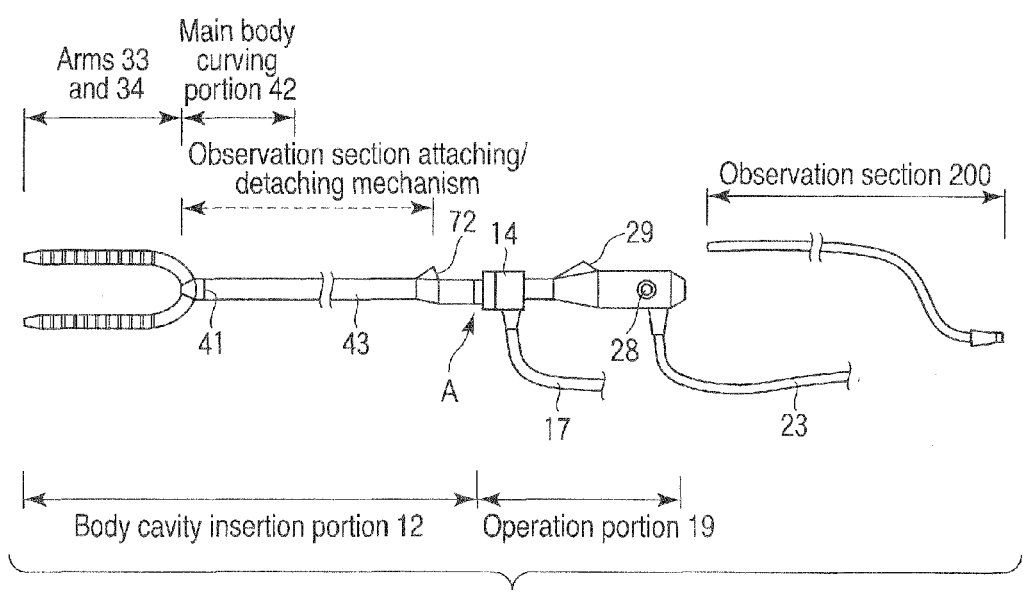
F I G. 20

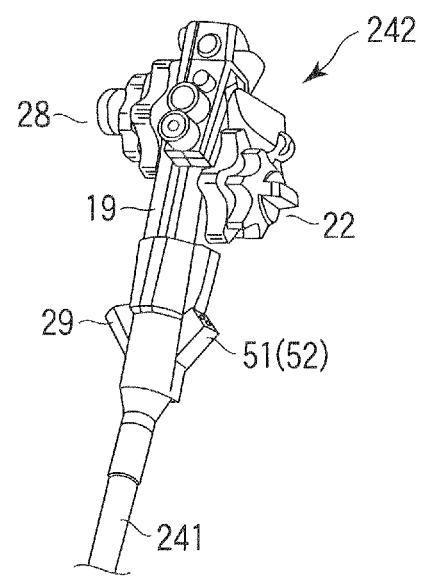
F I G. 23C

TREATMENT ENDOSCOPE

CROSS REFERENCE TO RELATED APPLICATIONS

This application is a Continuation Application of PCT Application No. PCT/JR2010/05455, filed Mar. 17, 2010 and based upon and claiming the benefit of priority from prior Japanese Patent Application No. 2009-068518, filed Mar. 19, 2009, the entire contents of all of which are incorporated herein by reference.

BACKGROUND OF THE INVENTION

1. Field of the Invention

The present invention relates to a treatment endoscope in which an arm equipped with a curving portion is provided in a state that the arm projects from a distal end of an insertion portion.

2. Description of the Related Art

Jpn. Pat. Appln. KOKAI Publication No. 2005-95590 has disclosed a treatment endoscope in which an arm equipped with a curving portion is provided at a distal end of an insertion portion which includes a curving portion and a flexible tube. In this treatment endoscope, the treatment arm equipped with the curving portion that projects from the distal end of the insertion portion conducts a treatment, such as cutting, removal, or stitching of a living tissue in a body cavity. According to the treatment endoscope, the living tissue in the body cavity can be lifted or moved by the treatment arm equipped with the curving portion that projects from the distal end of the insertion portion, thereby facilitating a relatively complicated treatment such as cutting, removal, or stitching.

BRIEF SUMMARY OF THE INVENTION

According to one aspect of the invention, a treatment endoscope includes that a body cavity insertion portion which includes a main body distal hard portion, and a main body curving portion provided to a proximal side of the main body distal hard portion; one or more treatment arm/arms projecting to a distal side from the main body distal hard portion of the body cavity insertion portion, each of the treatment arm/arms including a curving mechanism; an operation portion provided to the proximal side of the body cavity insertion portion; an observation section configured to image a field of view in a body cavity, the observation section including an imaging section provided within the main body distal hard portion of the body cavity insertion portion; an operation portion attaching/detaching mechanism configured to removably attach the operation portion to the body cavity insertion portion; an internal object which is extended to the proximal side from the body cavity insertion portion or from one of the treatment arm/arms through the operation portion attaching/detaching mechanism; and an observation section attaching/detaching mechanism configured to removably attach the observation section to the body cavity insertion portion. The operation portion attaching/detaching mechanism includes an internal object connection portion configured to connect the internal object to be separable into an insertion portion side part and an operation portion side part.

Advantages of the invention will be set forth in the description which follows, and in part will be obvious from the description, or may be learned by practice of the invention. Advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 2 is a schematic diagram showing the treatment endoscope according to the first embodiment;

FIG. 14A is a side view showing an attaching/detaching structure of the wires of the attaching/detaching portion in the treatment endoscope according to the fifth modification of the first embodiment before a connection chip is inserted into a connector;

FIG. 14B is a side view showing the attaching/detaching structure of the wires of the attaching/detaching portion in the treatment endoscope according to the fifth modification of the first embodiment in a state the connection chip is inserted in the connector at right angle;

FIG. 18 is a perspective view schematically showing an entire treatment endoscope according to a seventh modification of the first embodiment;

FIG. 19 is a schematic diagram showing the relation of elements that constitute an entire treatment endoscope according to a second embodiment of the present invention;

FIG. 20 is a schematic diagram showing the relation of elements that constitute an entire treatment endoscope according to a third embodiment of the present invention;

FIG. 23C is a perspective view schematically showing the treatment endoscope according to the sixth embodiment in a different direction from FIG. 23A and FIG. 23B.

DETAILED DESCRIPTION OF THE INVENTION

Embodiments of the present invention are described below. First, a treatment endoscope according to a first embodiment is described in detail with reference to FIG. 1 to FIG. 18.

Figure 1:
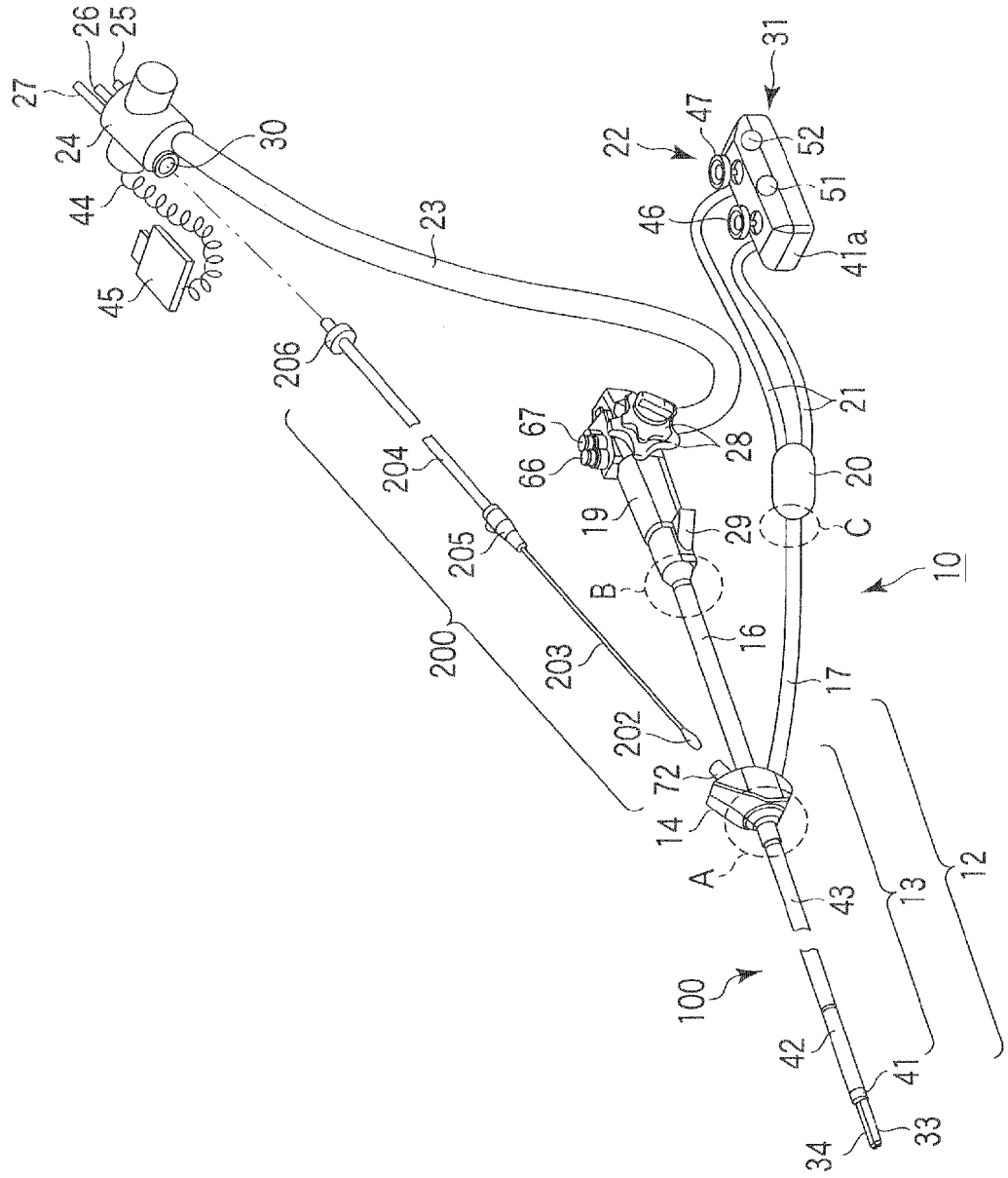
FIG. 1 is a perspective view schematically showing an entire treatment endoscope according to a first embodiment of the present invention.

As shown in FIG. 1 and FIG. 2, a treatment endoscope 10 according to the present embodiment includes an endoscope main body 100 and an observation unit (observation section) 200. The endoscope main body 100 includes a body cavity insertion portion 12 configured to be inserted into a body cavity, and a first branch 14 connected to a proximal end portion of the body cavity insertion portion 12. A first extension 16 and a second extension 17 are connected to a proximal side of the first branch 14. Each of the first extension 16 and the second extension 17 is formed from an elongated flexible tubular member, the first extension 16 and the second extension 17 branching from the first branch 14 and separately extending toward the proximal side. A first operation portion (main body operation portion) 19 is provided on the proximal side of the first extension 16. A second branch 20 is provided on the proximal side of the second extension 17, and two branch cables 21 are further extend toward the proximal side from the second branch 20. A second operation portion (arm operation portion) 22 is connected to the proximal end portions of the two branch cables 21. A universal cord 23 extending from the first operation portion 19 toward the proximal side is connected to the first operation portion 19. A link connector 24 is provided at a proximal end portion of the universal cord 23. The link connector 24 is provided with an air supply/water supply connection pipe 25, a suction pipe 26, and an illumination light guide pipe 27. The link connector 24 is detachably connected to an external console of, for example, a light source device. When the link connector 24 is connected to the external console of, for example, the light source device, the air supply/water supply connection pipe 25, the suction pipe 26, and the illumination light guide pipe 27 are connected to corresponding functional portions of a water supply source, a suction source, and a light source, respectively.

A signal cable 44 is connected to the link connector 24, and an imaging connector 45 is provided at a proximal end portion the signal cable 44. The imaging connector 45 is detachably connected to a camera control unit (not shown) which is another external console.

The first operation portion 19 is provided with a portion for an operator to grip by hand during an operation. The first operation portion 19 includes a curving operation knob (handle) 28 which is curving operation mechanism configured to curve a main body curving portion (described later) of the body cavity insertion portion 12, an insertion hole 29 of a treatment tool insertion channel, an air supply/water supply operation button 66 (described in detail later), a suction operation button 67, and a switch 68 configured to control the imaging action of the observation unit 200.

As shown in FIG. 1 and FIG. 2, the body cavity insertion portion 12 includes an insertion portion main body 13 which is a primary part, and at least one or more treatment arms 33 and 34 projecting from a distal end of the insertion portion main body 13 toward the distal side. As shown in FIG. 1 and FIG. 2, the insertion portion main body 13 includes a first hard portion (main body distal hard portion) 41 located at a most distal end side, a curving portion (main body curving portion) 42 connected to a proximal end portion of the first hard portion 41, and a flexible tube (main body flexible tube) 43 connected to a proximal end portion of the curving portion 42. The treatment arms 33 and 34 are supported on the distal end of the insertion portion main body 13 so that a proximal end portions thereof are coupled to the distal end of the insertion portion main body 13. The pair of treatment arms 33 and 34 are laterally arranged to project from the distal end of the insertion portion main body 13 toward the distal side. Here, the arrangement shown in FIG. 3 shows a waiting position.

Figure 3:
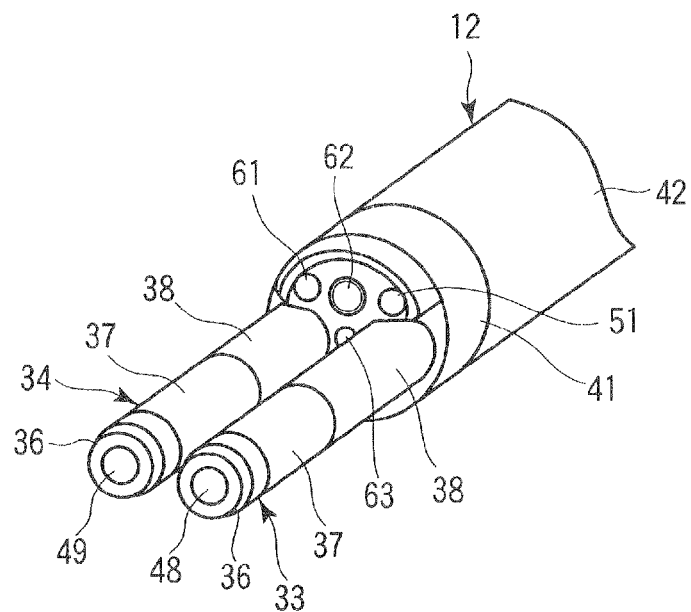
FIG. 3 is a perspective view showing arms provided at a distal end portion of the treatment endoscope according to the first embodiment in a state that the arms are located at a waiting position.

As shown in FIG. 2 and FIG. 3, each of the pair of treatment arms 33 and 34 includes a second hard portion (arm distal hard portion) 36 located at a most distal end side, a first curving portion (first arm curving portion) 37 connected to a proximal end portion of the second hard portion, and a second curving portion (second arm curving portion) 38 which is connected to a proximal end portion of the first curving portion 37 and which as its proximal end portion coupled to the distal end of the insertion portion main body 13. The first curving portion 37 and the second curving portion 38 can each include a curving mechanism similar to a curving portion of a general endoscope. In this case, operation wires are pushed or pulled by an operation unit 31 (described later) such that the first curving portion 37 and the second curving portion 38 are individually curved. For example, the first curving portion 37 is configured to curve in four directions, and the second curving portion is configured to curve in two directions.

Figure 4:
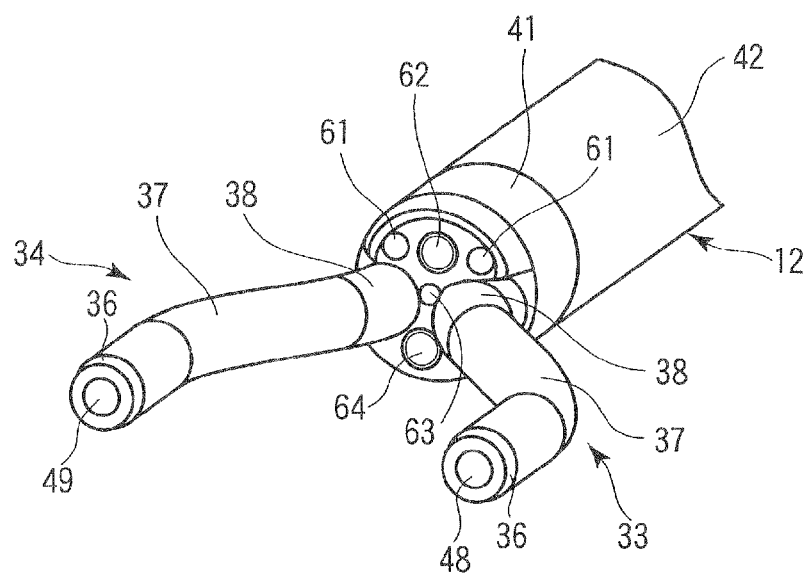
FIG. 4 is a perspective view showing the arms provided at the distal end portion of the treatment endoscope according to the first embodiment in a state that the arms are outstretched.

As shown in FIG. 1, the operation unit 31 is provided with two operation handles 46 and 47 corresponding to the treatment arms 33 and 34. The two operation handles 46 and 47 are provided so that the treatment arms 33 and 34 are separately curved. The two curving portions 37 and 38 of the corresponding arms 33 and 34 are individually operated by the operation handles 46 and 47, respectively. That is, the curving portions 37 and 38 of the arm 33 can be individually operated by the operation of the operation handle 46. The two curving portions 37 and 38 of the arm 34 can be individually operated by the operation of the operation handle 47. FIG. 3 shows a waiting condition in which the curving portions 37 and 38 of the right and left arms 33 and 34 are not curved. FIG. 4 shows one condition during a treatment in which the curving portions 37 and 38 of the right and left arms 33 and 34 are curved and the right and left arms 33 and 34 are laterally outstretched.

In the endoscope main body 100, the above-mentioned curving operation wires (not shown) extend in the insertion portion main body 13 from the second operation portion 22 through the branch cables 21, 21 and the second extension 17, and the distal ends of the curving operation wires are connected to the arms 33 and 34. If the operation handles 46 and 47 of the second operation portion 22 are operated to pull the respective curving operation wires, the curving mechanisms of the treatment arms 33 and 34 corresponding to the respective curving operation wires are driven, and the curving portions 37 and 38 of the treatment arms 33 and 34 can be curved.

Treatment tool guide channels (two treatment tool guide channels in the present embodiment) corresponding in number to the arms 33 and 34 are formed in the body cavity insertion portion 12. The treatment tool guide channels are extended to the branch cable 21 from the arms 33 and 34 through the insertion portion main body 13, the second extension 17, and the second branch 20. One of the treatment tool guide channels is in communication with a first channel opening 48 formed at a distal end of the arm 33 corresponding to this treatment tool guide channel. The other treatment tool guide channel is in communication with a second channel opening 49 formed at a distal end of the arm 34 corresponding to this treatment tool guide channel (see FIG. 3 and FIG. 4).

As shown in FIG. 1, the main body of the operation unit 31 is provided with a first insertion hole 51 to be in communication with the treatment tool guide channel corresponding to one treatment arm 33, and a second insertion hole 52 to be in communication with the treatment tool guide channel corresponding to the other treatment arm 34. These channels can be not only used to insert or remove an arm treatment tool but also used in other purposes such as the supply of water from the distal ends of the arms 33 and 34 to the body cavity, the injection of a chemical, and suction.

Figure 5:
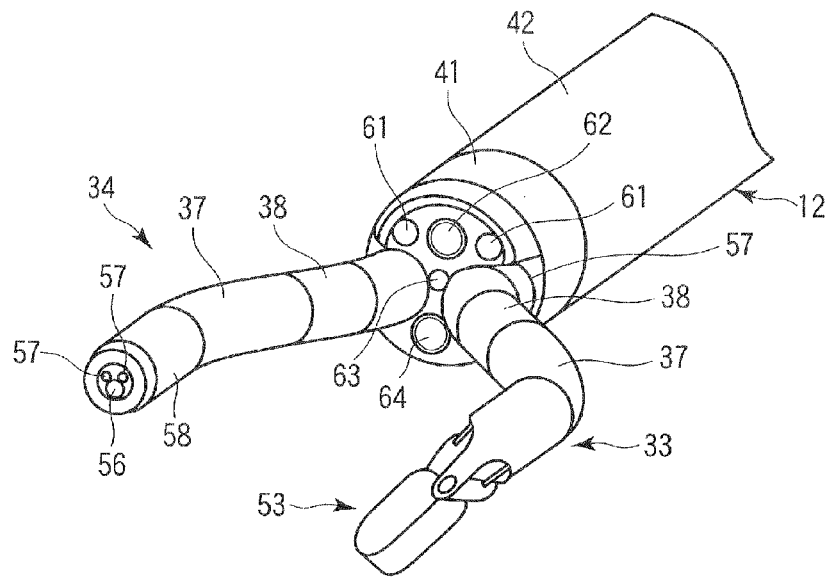
FIG. 5 is a perspective view showing arms provided at a distal end portion of a treatment endoscope according to a first modification of the first embodiment in a state that the arms are outstretched.

In the embodiment described above, the first treatment arm 33 and the second treatment arm 34 are treatment arms including openings formed to be in communication with the treatment tool guide channels. However, for example, as a first modification, a treatment portion 53 in the form of, for example, a forceps may be formed at the distal end portion of the first treatment arm 33, and an observation function section 58 provided with an observation section 56 and illumination holes 57 may be formed at the distal end portion of the second treatment arm 34, as shown in FIG. 5.

As shown in FIG. 3 and FIG. 4, a pair of illumination windows 61, an observation window opening 62, an air supply/water supply nozzle 63, and an insertion portion main body channel hole 64 are provided in a distal face of the body cavity insertion portion 12. A distal end portion of an imaging unit (imaging section) 202 of the observation unit 200 (described later) is disposed in the observation window opening 62. The air supply/water supply nozzle 63 supplies air or water to a distal end of the imaging unit 202 disposed in the observation window opening 62. The pair of illumination windows 61, the observation window opening 62, the air supply/water supply nozzle 63, and the insertion portion main body channel hole 64 are located off the first treatment arm 33 and the second treatment arm 34. The illumination windows 61 are provided with distal lenses doubling as transparent covers. The observation window opening 62 may be an open bore pierced the distal side, or may be an observation window in which an opening is blocked with a transparent cover.

As shown in FIG. 1 and FIG. 2, the observation unit 200 includes an insertion portion 203 provided with the imaging unit 202 at its most distal end, a cable unit 204 connected to a proximal end portion of the insertion portion 203, and an observation unit connector 206 connected to a proximal end portion of the cable unit 204. An engagement portion 205 is provided between the insertion portion 203 and the cable unit 204. The insertion portion 203 is a portion to be inserted into an insertion passage 71 formed in the endoscope main body 100. When the insertion portion 203 is inserted into the insertion passage 71 up to a predetermined position, the engagement portion 205 engages with an insertion bore 72 of the insertion passage 71. At the same time, the imaging unit 202 is held at a predetermined position, and the imaging unit 202 is fixedly attached to the observation window opening 62. As a result, observation section attaching/detaching mechanism configured to attach/detach the unit (imaging section) 202 to/from the body cavity insertion portion 12 is formed.

The observation unit connector 206 is connected to be inserted in an insertion hole 30 formed in the link connector 24. When the imaging unit 202 is attached to the endoscope main body 100 in use, an image signal obtained by imaging in the imaging unit 202 is sent to the camera control unit from the link connector 24 through the signal cable 44. The image signal is converted to a video signal by the camera control unit, and an observation image is displayed on an unshown monitor.

Now, the structure of the observation section attaching/detaching mechanism configured to attach/detach the observation unit 200 to/from the endoscope main body 100 is specifically described. As shown in FIG. 2, the insertion passage (path) 71 to inserted the observation unit 200 is formed in the body cavity insertion portion 12. Moreover, insertion guide mechanism and observation unit attaching/detaching mechanism (observation section attaching/detaching mechanism) are provided to insert the insertion portion 203 of the observation unit 200 to the insertion passage 71 and removably attach the observation unit 200 to the body cavity insertion portion 12.

Here, a distal end of the insertion passage 71 is in communication with the observation window opening 62, and a proximal end of the insertion passage 71 is in communication with the insertion bore 72 formed in the first branch 14. In the body cavity insertion portion 12, the insertion passage 71 is isolated from other internal objects. That is, the insertion passage 71 is formed in the body cavity insertion portion 12 to be partitioned by, for example, a tube or a partition member. The cross-sectional shape of the insertion bore 72 corresponds to the cross-sectional shape of the imaging unit 202. Thus, the imaging unit 202 is inserted into the insertion passage 71 in a state that a posture of the imaging unit 202 is set, and the insertion portion 203 of the observation unit 200 is guided into the insertion passage 71 in the state that the posture of the imaging unit 202 is set. That is, the imaging unit 202 forms posture regulating mechanism configured to guide the insertion portion 203 of the observation unit 200 into the insertion passage 71 in the state that the posture of the imaging unit 202 is set. A storage room configured to position the imaging unit 202 in accordance with the observation window opening 62 is formed at the distal end portion of the insertion passage 71. This storage room is also provided with posture regulating mechanism configured to regulate the posture of the imaging unit 202 to place. The middle part of the insertion passage 71 is preferably formed of, for example, a flexible and expansive/contractive tube, and isolated from other internal objects.

The endoscope main body 100 includes various internal objects therein. The internal objects include, for example, not only a guide tube configured to guide the observation unit 200 but also channel tubes that respectively form channels, wires which are curving operation members configured to operate the curving portion 42 of the insertion portion main body 13 and curving mechanisms of the curving portions 37 and 38 of the treatment arms 33 and 34, guide members configured to guide these wires, an air supply/water supply tube in communication with the air supply/water supply nozzle 63, a tube that forms the treatment tool insertion channel in communication with the channel hole 64, a suction tube in communication with the treatment tool insertion channel, a light guide configured to guide illumination light to the illumination windows 61, and a conductive wire such as a signal line.

The tube that forms the treatment tool insertion channel in communication with the channel hole 64 is guided to the insertion hole 29 of the first operation portion 19 from the first hard portion 41 of the insertion portion main body 13 through the curving portion 42, the flexible tube 43, the first branch 14, and the first extension 16. The tubes that form the channels 48 and 49 of the treatment arms 33 and 34 are guided to the first branch 14 from the treatment arms 33 and 34 through the first hard portion 41, the curving portion 42, and the flexible tube 43 of the insertion portion main body 13. These tubes are further guided to the first insertion hole 51 and the second insertion hole 52 of the operation unit 31 of the second operation portion 22 from the first branch 14 through the second extension 17, the second branch 20, and the branch cables 21. The wire of operating the curving mechanism of the curving portion 42 of the insertion portion main body 13 is guided to the first operation portion 19 from the curving portion 42 through the flexible tube 43, the first branch 14, and the first extension 16. The wires of operating the curving mechanisms of the curving portions 37 and 38 of the treatment arms 33 and 34 are guided to the operation unit 31 of the second operation portion 22 from the treatment arms 33 and 34 through the first hard portion 41, the curving portion 42, and the flexible tube 43 of the insertion portion main body 13, the first branch 14, the second extension 17, the second branch 20, and the branch cables 21. The air supply/water supply tube in communication with the air supply/water supply nozzle 63 is guided to the first branch 14 from the air supply/water supply nozzle 63 through the first hard portion 41, the curving portion 42, and the flexible tube 43 of the insertion portion main body 13. The air supply/water supply tube is further connected to the air supply/water supply connection pipe 25 of the link connector 24 through the first branch 14, the first extension 16, the first operation portion 19, and the universal cord 23.

The air supply/water supply to the air supply/water supply nozzle 63 is controlled by a switching valve (not shown), and this switching valve is operated by an air supply/water supply operation button 66 provided in the first operation portion 19. In the first operation portion 19, the treatment tool insertion channel 64 is connected in a state that the treatment tool insertion channel 64 is in communication with the suction tube via a switching valve (not shown) partway. This suction tube is connected to the suction pipe 26 of the link connector 24 through the first operation portion 19 and the universal cord 23. The suction tube is connected to or disconnected from the channel 64 under the control of a switching valve provided in the first operation portion 19, and this switching valve is operated by the suction operation button 67. The light guide of guiding the illumination light to the illumination windows 61 includes a fiber bundle. This light guide is connected to the illumination light guide pipe 27 of the link connector 24 through the first hard portion 41, the curving portion 42, the flexible tube 43, the first branch 14, the first extension 16, the first operation portion 19, and the universal cord 23. The guide members of guiding the wires as the curving operation members includes, for example, guide rings and guide tubes. The internal objects include, in addition to those mentioned above, various internal members known in a general endoscope.

Now, operation portion attaching/detaching mechanism that enables the operation portion of the treatment endoscope to be attached or removed through the body cavity insertion portion is described. As shown in FIG. 1, the operation portion attaching/detaching mechanism is provided at a connection portion A configured to connect the body cavity insertion portion 12 to the first branch 14, connection portion B configured to connect the first operation portion 19 to the first extension 16, or a connection portion C configured to connect the second branch 20 to the second extension 17. However, the place of the connection portion and the number of the connection portions are not limited; for example, connection portions are provided partway in the extensions 16 and 17. Moreover, it is not necessary to provide all the connection portions A, B, and C. However, if the body cavity insertion portion 12 is configured to be separated from a side of the operation portion at the connection portion A (operation portion integral attaching/detaching mechanism), the operation portions 19 and 22 can be collectively removed from a side of the body cavity insertion portion. When the operation portion attaching/detaching mechanism is provided at the connection portion (main body operation portion attaching/detaching mechanism) B, the first operation portion 19, the universal cord 23, and the link connector 24, for example, can be removed from the side of the body cavity insertion portion 12. When the operation portion attaching/detaching mechanism is provided at the connection portion (arm operation portion attaching/detaching mechanism) C, the second branch 20, the branch cables 21, and the second operation portion 22 can be removed from the side of the body cavity insertion portion 12.

Figure 6:
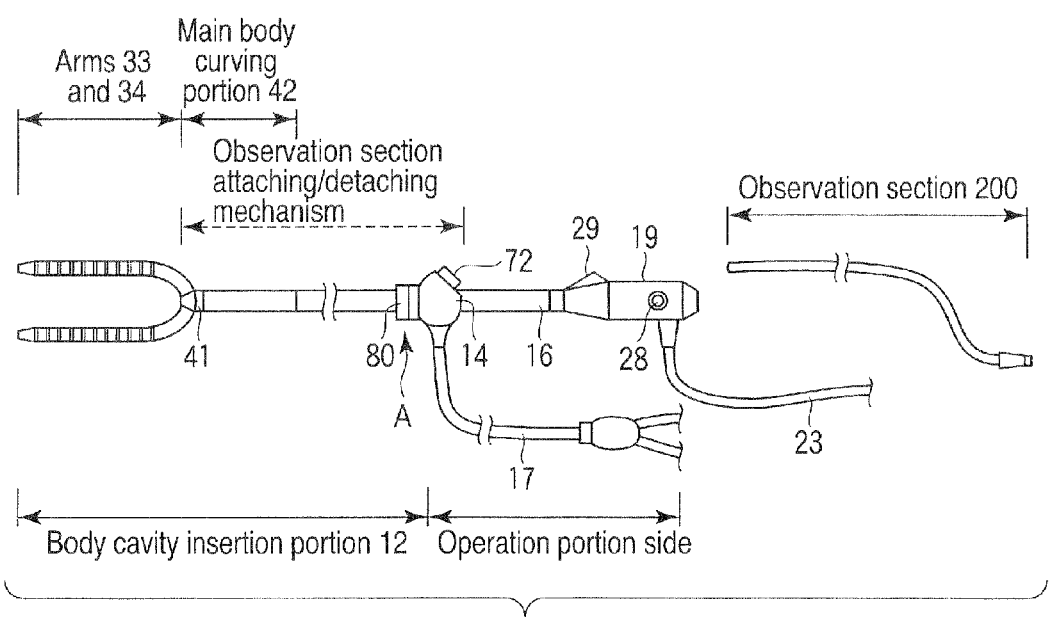
FIG. 6 is a schematic diagram showing the relation of elements that constitute the entire treatment endoscope according to the first embodiment.

FIG. 6 is an explanatory diagram schematically showing a configuration in which an operation portion attaching/detaching portion 80 is provided at the connection portion A which connects the body cavity insertion portion 12 to the first branch 14.

Figure 7:
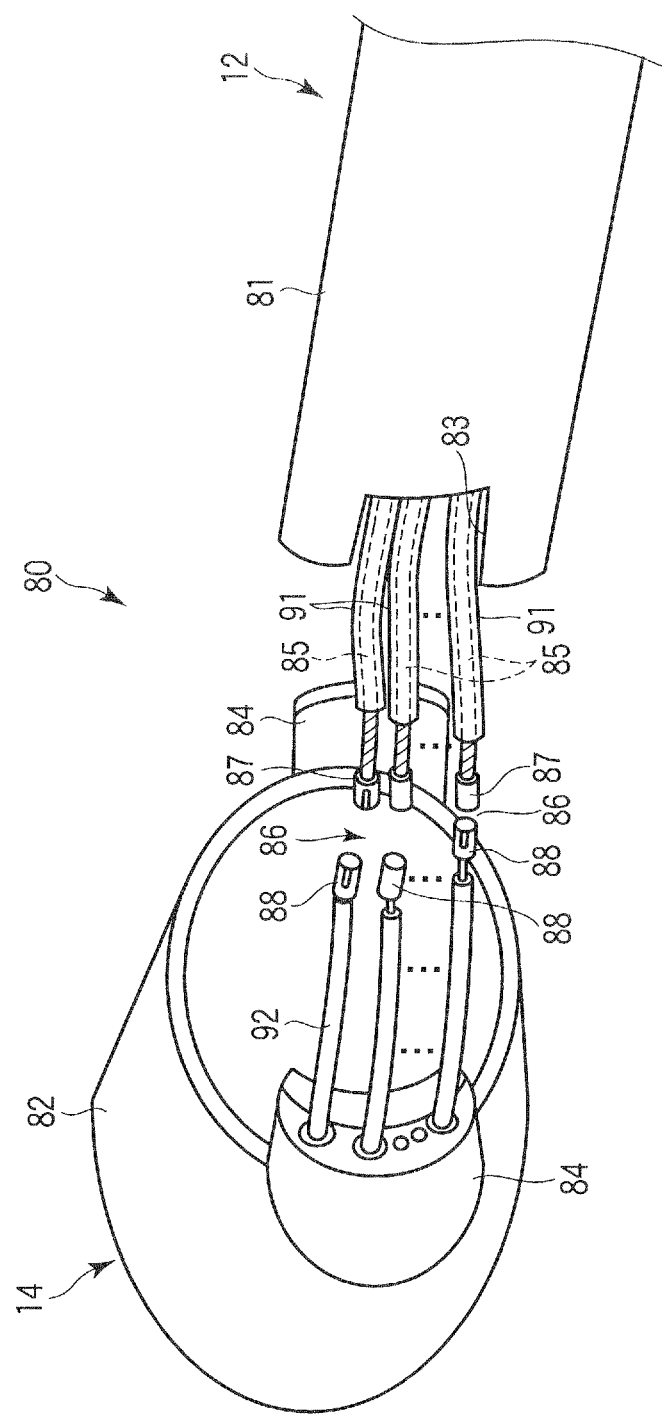
FIG. 7 is a perspective view schematically showing an attaching/detaching portion of the treatment endoscope according to the first embodiment in a separated state.
Figure 8:
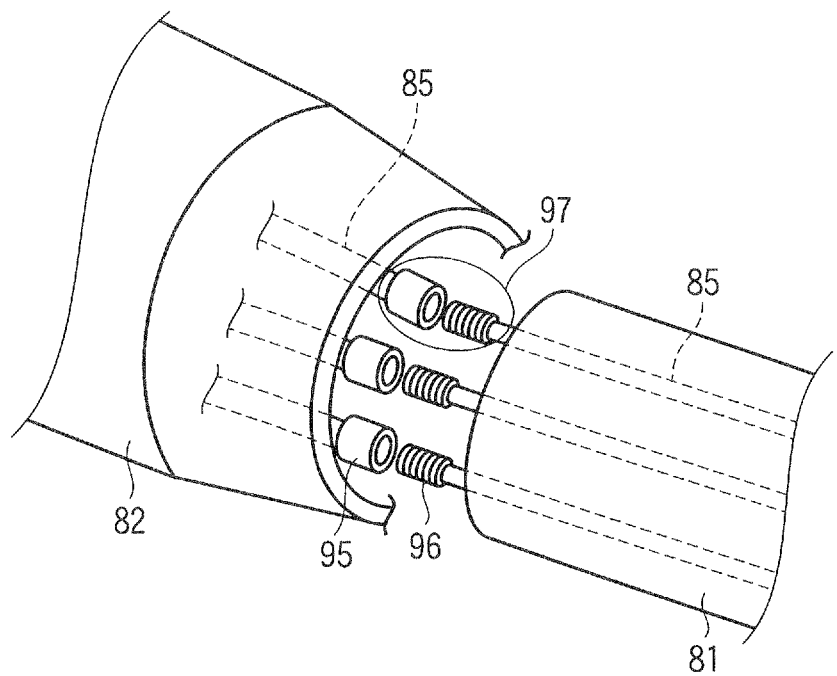
FIG. 8 is a perspective view schematically showing an attaching/detaching portion of a treatment endoscope according to a second modification of the first embodiment in a separated state.
Figure 9:
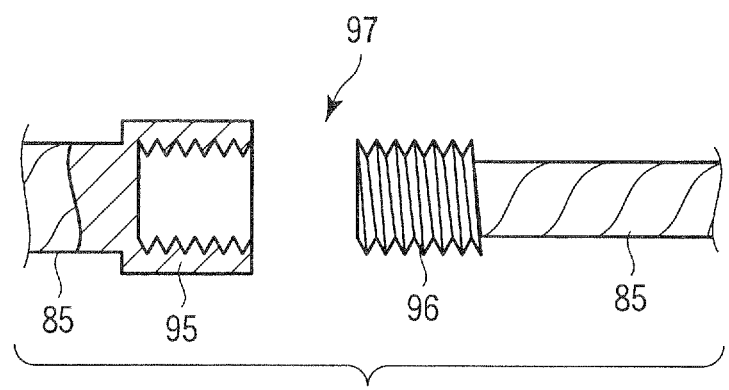
FIG. 9 is a partially sectional side view of an attaching/detaching structure of wires of the attaching/detaching portion in the treatment endoscope according to a second modification of the first embodiment.

As shown in FIG. 7, in the operation portion attaching/detaching portion 80, for example, an exterior member 81 of the insertion portion main body 13 is detachably coupled to an exterior member 82 of the first branch 14. Various structures are conceivable to detachably couple these members 81 and 82 together. When the members 81 and 82 are coupled together, the members 81 and 82 are preferably fixed at predetermined positions and airtightly coupled. In an example shown in FIG. 7, cut recesses 83 are provided in the exterior member 81 of the insertion portion main body 13, and projections 84 shaped to fit into the cut recesses 83 are provided in the exterior member 82 of the first branch 14. The projections 84 fit into the cut recesses 83 to determine a junction position. For example, the following mechanism configured to fix the members 81 and 82 are conceivable: mechanism configured to couple the members 81 and 82 so that an engagement portion provided in one of the members 81 and 82 is engaged with a receiving portion provided in the other member, mechanism configured to couple the members 81 and 82 by screws, or clamp mechanism.

Each of the internal objects located within the operation portion attaching/detaching portion 80 is provided with connection portions that permit disconnection. The example shown in FIG. 7 shows connection portions of wires 85. The wires 85 are provided with push-on turn-off joint portions 86 which are connection portions that permit the wires 85 to be disconnected partway. In the joint portion 86, a first connection fitting 87 is provided at the proximal end of a wire portion located on the insertion portion main body side of the wires 85, and a second connection fitting 88 is provided at the distal end of a wire portion on the operation portion side of the wires 85. In such a configuration, the detachable joint portion 86 is formed by the first connection fitting 87 and the second connection fitting 88. One of the first connection fitting 87 and the second connection fitting 88 is inserted into the other to automatically lock and connect the first connection fitting 87 and the second connection fitting 88. In order to separate the first connection fitting 87 and the second connection fitting 88 from each other, an unlock ring (not shown), for example, provided in one of the connection fittings 87 and 88 is rotated. As a result, the first connection fitting 87 and the second connection fitting 88 are unlocked and separated from each other. Each of the wires 85 is inserted through wire sheathes (guide members) 91 and 92 to the distal side and proximal side regions of each of joint portions 86 (regions other than the joint portion 86). As a result, the wires 85 are guided.

When the treatment endoscope 10 is in use, the observation unit 200 is combined with the body cavity insertion portion 12. The curving portion 42 of the insertion portion main body 13 can be curved by operating the curving operation knob 28 of the first operation portion 19. The first treatment arm 33 and the second treatment arm 34 can be curved by operating the operation unit 31 of the second operation portion 22. In other respects, the treatment endoscope 10 can be operated in the same manner as general endoscopes.

After use, the observation unit 200 and the operation portion side are separated from the side of the body cavity insertion portion 12, and the body cavity insertion portion 12 is independently cleaned and sterilized. The body cavity insertion portion 12 is replaced if necessary from the viewpoint of its durability, and the components on the side of the operation portion are reused. Therefore, parts on the side of the body cavity insertion portion 12 including the treatment arms 33 and 34 are separated, and the remaining components on the side of the operation portion can be reused. Consequently, as compared with the case where the whole treatment endoscope 100 is disposed of, an operation cost of every use of the treatment endoscope can be reduced.

Furthermore, in the treatment endoscope 100 of the present invention, both the first treatment arm 33 and the second treatment arm 34 are supported on the distal end of the insertion portion main body 13. Therefore, the first treatment arm 33 and the second treatment arm 34 follow the motion of the distal end of the insertion portion main body 13. Thus, when the curving portion 42 of the insertion portion main body 13 is curved, the first treatment arm 33 and the second treatment arm 34 move in accordance with the motion of the curving portion 42. That is, the first treatment arm 33 and the second treatment arm 34 move with reference to the distal end of the insertion portion main body 13. In this way, the first treatment arm 33 and the second treatment arm 34, which are treatment action arms, are supported to move to follow the distal end of the insertion portion main body 13. Therefore, the observation unit 200 disposed in the first hard portion. (main body distal hard portion) 41 at the distal end of the insertion portion main body 13 can capture the first treatment arm 33 and the second treatment arm 34 in the view field of the observation unit 200 to follow the motions of the first treatment arm 33 and the second treatment arm 34. Consequently, the observation unit 200 can continue observation while following the first treatment arm 33 and the second treatment arm 34. Even if the first treatment arm 33 and/or the second treatment arm 34 are/is out of the view field of the observation unit 200, the first treatment arm 33 and the second treatment arm 34 are supported on the distal end of the insertion portion main body 13 and therefore do not independently move out of the view field of the observation unit 200. As a result, the first treatment arm 33 and/or the second treatment arm 34 can be easily brought back into the view field of the observation unit 200. Thus, the treatment conducted by the first treatment arm 33 and the second treatment arm 34, which are the treatment action arms, can be basically kept under observation. This facilitates and ensures the treatment in the body cavity, and allows a treatment to be rapidly and accurately conducted by the first treatment arm 33 and the second treatment arm 34.

Now, a modification of the present embodiment is described. Various forms of joints are conceivable besides the above-mentioned joints as forms of connections that allow the wires 85 to be disconnected partway. In a second modification shown in FIG. 8 and FIG. 9, a first connection fitting 95 in the form of a nut (internal screw) is provided on one connection fitting, and a second connection fitting 96 in the form of an external screw is provided on the other connection fitting. The first connection fitting 95 and the second connection fitting 96 are then removably screwed together, so that a connection portion 97 is formed.

Figure 10:
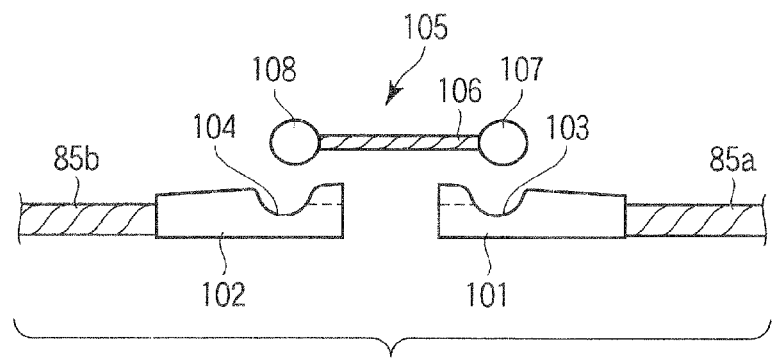
FIG. 10 is a side view showing an attaching/detaching structure of wires of an attaching/detaching portion in a treatment endoscope according to a third modification of the first embodiment.

FIG. 10 shows a third modification of the form of connecting the wires configured to be disconnected partway. In the connection form according to this modification, a first connector 101 including a recessed receiving portion 103 is provided at a proximal end of an insertion portion main body side wire 85a of the disconnected wires, and a second connector 102 also including a recessed receiving portion 104 is provided at the distal end of an operation portion side wire 85b. The first connector 101 and the second connector 102 are then removably coupled together by a coupler 105 (described later). The coupler 105 includes a coupling wire 106, a spherical connector 107, and a spherical connector 108. The connector 107 is provided at one end of the coupling wire 106, and removably fitted into the receiving portion 103 of the first connector 101. The connector 108 is provided at the other end of the coupling wire 106, and removably fitted into the receiving portion 104 of the second connector 102. The coupler 105 is attached to or detached from the first connector 101 and the second connector 102 so that the wire is coupled in a separable manner.

Figure 11A:
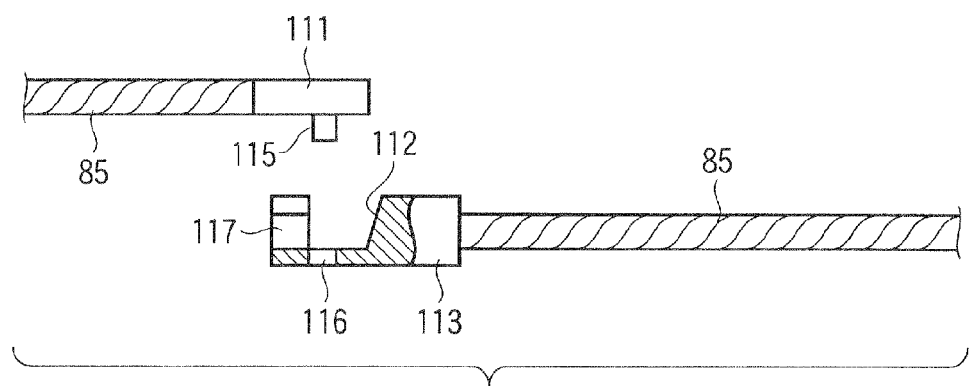
FIG. 11A is a partially sectional side view showing an attaching/detaching structure of wires of an attaching/detaching portion in a treatment endoscope according to a fourth modification of the first embodiment in a state that the wires are separated.
Figure 11B:
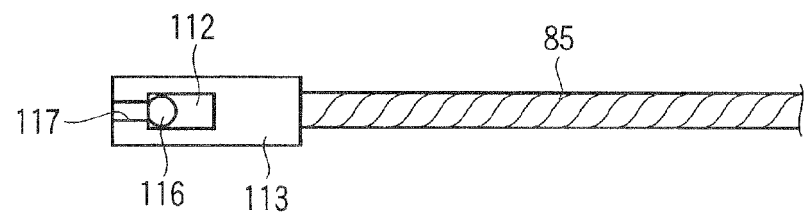
FIG. 11B is a plan view showing one side of the attaching/detaching structure of the wires of the attaching/detaching portion in the treatment endoscope according to the fourth modification of the first embodiment.
Figure 12:
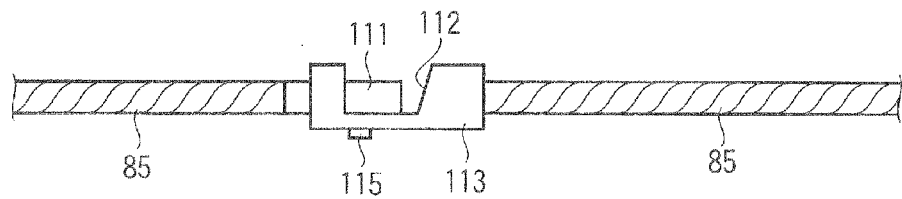
FIG. 12 is a side view showing the attaching/detaching structure of the wires of the attaching/detaching portion in the treatment endoscope according to the fourth modification of the first embodiment in a state that the wires are coupled.

FIG. 11A to FIG. 12 show a fourth modification of the form of connecting the wires configured to be disconnected partway. In the connection form according to this modification, a columnar connection chip 111 is provided at one separation end of the wire 85 configured to be disconnected partway. A connector 113 including a recess 112 into which the connection chip 111 is fitted is provided at the other separation end of the wire 85. A lock pin 115 is provided on the side surface of the connection chip 111. The lock pin 115 is locked when fitted in a lock hole 116 formed in the bottom surface of the recess 112. A holding portion 117 is formed at a distal end portion of the connector 113. A proximal end portion of the connection chip 111 is held in the holding portion 117 when the connection chip 111 is fitted in the recess 112.

In order to connect the connection chip 111 to the connector 113, the connection chip 111 is aligned with and thus inserted into the recess 112 from the side of the connector 113 where the recess 112 is open, as shown in FIG. 11A. Further, as shown in FIG. 12, the connection chip 111 is fitted into the recess 112, and the lock pin 115 is fitted in and thus locked by the lock hole 116, and the connection chip 111 is held by the holding portion 117. Moreover, as described later in a fifth modification with reference to FIG. 14A to FIG. 14D, the connection chip 111 may be connected to a predetermined position of the recess 112 by inserting the distal end of the connection chip 111 into the recess 112 of the connector 113 at right angles, and tilting the connection chip 111 so that the axial center of the connection chip 111 is aligned with the axial center direction of the connector 113. The connection chip 111 can be separated from the connector 113 by performing the above-described procedure in reverse order.

Figure 13:
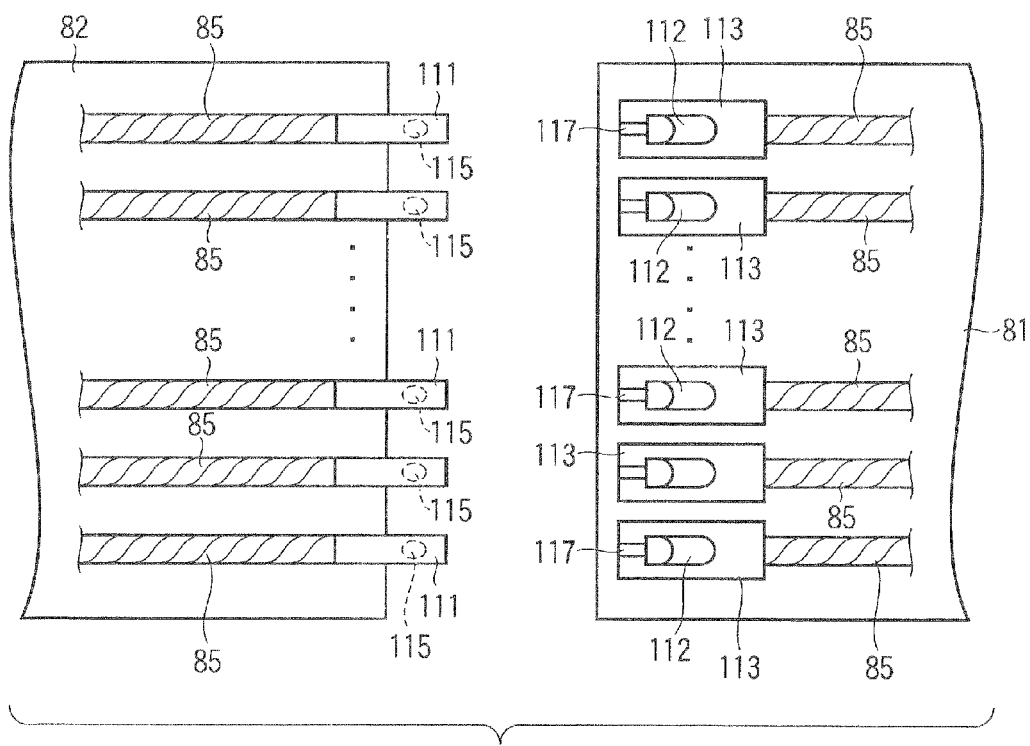
FIG. 13 is a schematic diagram showing an attaching/detaching portion in a treatment endoscope according to a fifth modification of the first embodiment in a state that wires are separated.

FIG. 13 shows the form according to the fifth modification in which connection mechanism of the wires in FIG. 11 and FIG. 12 can be disconnected all together. In the present modification, for example, as shown in FIG. 13, the connectors 113 corresponding to the respective wires 85 are arranged side by side in the exterior member 81 of the insertion portion main body 13 or in another member incorporated in the exterior member 81. On the other hand, the connection chips 111 are arranged side by side at positions corresponding to the connectors 113 in, for example, the exterior member 82 of the first branch 14 or in another member incorporated in the exterior member 82. According to such a configuration, the connection chips 111 can be easily attached to or detached from the connectors 113 all together in the wires 85. That is, all the wires 85 can be combined together by the combining procedure shown in FIG. 14A to FIG. 14D.

Figure 14C:
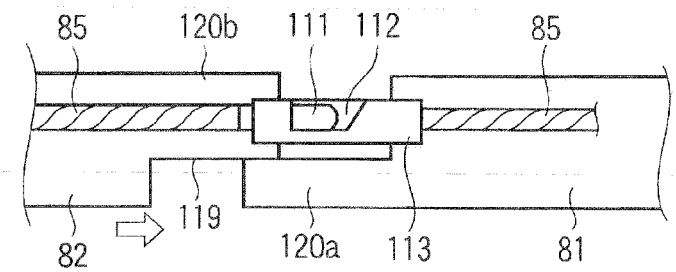
FIG. 14C is a side view showing the attaching/detaching structure of the wires of the attaching/detaching portion in the treatment endoscope according to the fifth modification of the first embodiment in a state that the connection chip is tilted so that an axial center of the connection chip is aligned with an axial center direction of the connector.
Figure 14D:
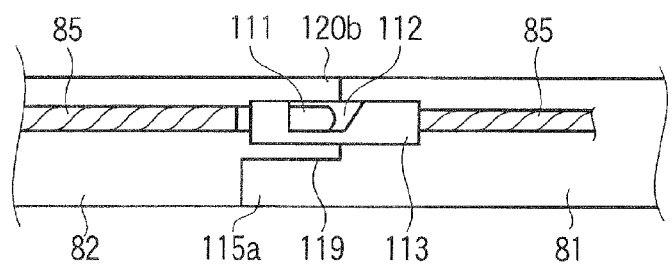
FIG. 14D is a side view showing the attaching/detaching structure of the wires of the attaching/detaching portion in the treatment endoscope according to the fifth modification of the first embodiment in a state that pieces that form steps are fitted together.

Steps 119 to be toothed with each other are formed in butt portions between the exterior member 81 of the insertion portion main body 13 and the exterior member 82 of the first branch 14. The exterior members 81 and 82 are coupled together by fitting together pieces 120a and 120b that form the steps 119, as shown in FIG. 14D.

Figure 15A:
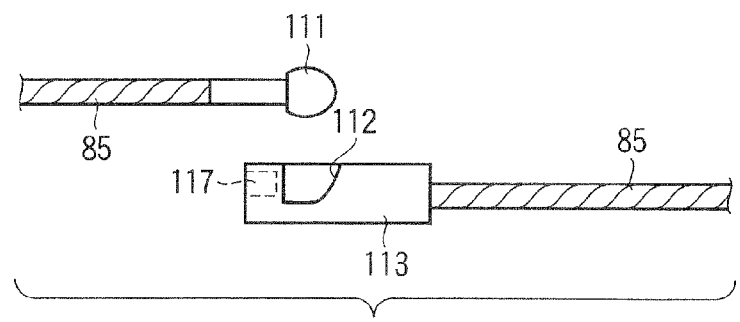
FIG. 15A is a side view showing an attaching/detaching structure of wires of an attaching/detaching portion in a treatment endoscope according to a sixth modification of the first embodiment in a separated state.
Figure 15B:
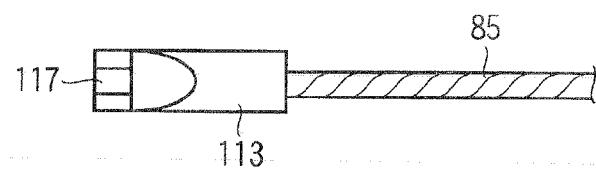
FIG. 15B is a plan view showing one side of the attaching/detaching structure of the wires of the attaching/detaching portion in the treatment endoscope according to the sixth modification of the first embodiment.
Figure 16:
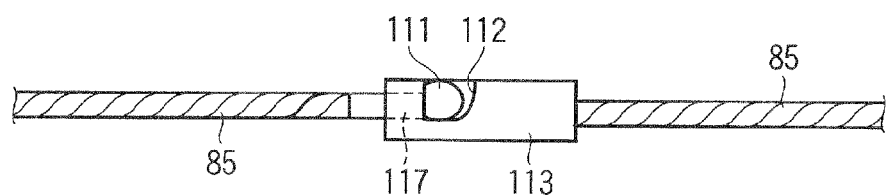
FIG. 16 is a side view showing the attaching/detaching structure of the wires of the attaching/detaching portion in the treatment endoscope according to the sixth modification of the first embodiment in a coupled state.

FIG. 15A to FIG. 16 show a sixth modification of the connection mechanism of the wires in FIG. 11 and FIG. 12. In this modification, one of the connectors is a spherical connection chip 111, and the other connector 113 with which the connection chip 111 is engaged is provided with a recess 112 into which the connection chip 111 is fitted.

Figure 17:
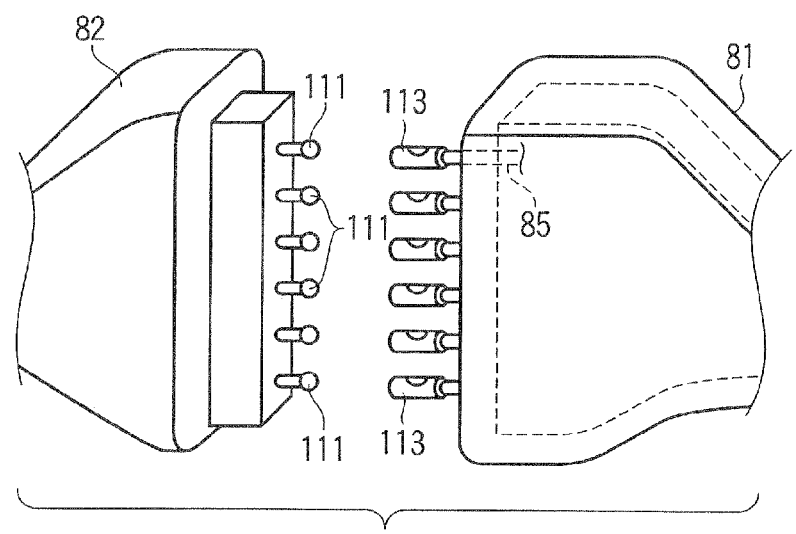
FIG. 17 is a perspective view showing the wires of the attaching/detaching portion in the treatment endoscope according to the sixth modification of the first embodiment in a state that the wires are separated.

As shown in FIG. 17, the connection chips 111 corresponding to the respective wires are arranged side by side in, for example, the exterior member 82 of the first branch 14 or in another member incorporated in the exterior member 82. The connectors 113 corresponding to the respective connection chips 111 are arranged side by side in, for example, the exterior member 81 of the insertion portion main body 13 or in another member incorporated in the exterior member 81. Thus, the connection chips 111 corresponding to the respective wires can be collectively attached to or detached from the connectors 113.

While the forms of connecting the wires in a separable manner have been described above, forms of separable connection portions are also provided to correspond to the kinds of internal objects other than the wires incorporated at separation places. For example, detachable connection portions that use known fluid couplings (pipe joints) are provided to correspond to the tubes that form the channels. In the detachable tube connection portion, a plug is provided in one tube separation end, and a socket is provided in the other tube separation end. The plug and the socket are coupled together without separating from each other by putting the plug into the socket (plug-in form) (in this case, it is preferable to taper fitting parts and fit the tapered parts together.) Alternatively, the separation ends of two tubes may be coupled together in a screw-in form. In this case, the parts to be connected are kept connected by fastening mechanism such as fastening rings. The connection portions are not exclusively configured so that one tube separation end is directly coupled to the other tube separation end. The separation ends may be indirectly connected to each other via another relay connector.

An internal object such as the light guide configured to guide the illumination light may also be provided with a separable connection portion partway. For example, one light guide separation end face is abutted to the other light guide separation end face to form a connection portion. Alternatively, the light guide separation end faces may be coupled and fixed together without separating from each other by coupling mechanism such as rings so that another light guide member intervenes between the light guide separation end faces. Alternatively, a coupling that detachably connects known light guides may be used to form a separable connection portion. In this case as well, one separation end and the other separation end are not exclusively directly coupled together and may be indirectly connected to each other via another relay connector. Moreover, instead of being disconnected partway, the light guide of guiding the illumination light may be able to be detachably inserted into the side of the body cavity insertion portion 12 in the same manner as the observation unit.

Furthermore, for an electric wire such as a signal line, coupling mechanism that permits, for example, known separation ends such as a plug and a socket to be conductively connected to each other may be used. Moreover, plug-in connection mechanism that puts the plug into the socket may be provided. Further, a connection form similar to the above-mentioned forms of connecting the wires in a separable manner may be used. In this case as well, one separation end and the other separation end are not exclusively directly coupled together and may be indirectly connected to each other via another relay connector.

In the embodiment and its modifications described above, in order to separate the body cavity insertion portion side of the treatment endoscope from the operation portion side, the connection portion is provided to disconnect the internal object partway and to detachably connect the separation ends together at a position corresponding to a part to be disconnected. However, no connection portion that enables the disconnection of the internal object may be provided at the place to separate the operation portion side from the body cavity insertion portion side. For example, in the part of the treatment endoscope to be disconnected, the internal object may be extended to the proximal side from the side of the body cavity insertion portion 12, and the above-mentioned separable connection portion (attaching/detaching portion) may be provided partway on the part of the internal object extended to the proximal side. Moreover, at the place where the operation portion side is separated from the body cavity insertion portion side, the internal object may be extended to the proximal side from the body cavity insertion portion side, and the proximal end of the internal object extended to the proximal side may be detachably connected to, for example, a member or device to be attached to the internal object. FIG. 18 is a diagram showing a seventh modification which is one such example. In this modification, an internal object such as an air supply tube, a water supply tube, or a suction tube extended from the body cavity insertion portion side to the console device 119 is extended to the proximal side of the body cavity insertion portion. The extending portion of the internal object is removably coupled to a connection target of the internal object. That is, an internal object cable 118 is extended to the proximal side of the insertion portion main body 13 through the first branch 14 without being separated from the side of the body cavity insertion portion 12. The internal object cable 118 is detachably connected to the console device 119 corresponding to the internal object. When an internal object such as an air supply tube, a water supply tube, or a suction tube is extended to the proximal side of the body cavity insertion portion without being separated partway, the air supply/water supply operation button, the suction operation button, or switches provided in the first operation portion 19 may be placed on the side of the console device 119.

FIG. 19 is a diagram schematically showing a configuration according to a second embodiment of the present invention. In the present embodiment, observation section attaching/detaching mechanism (insertion passage) 71 to insert an insertion portion 203 of an observation unit 200 is extended to a first operation portion 19 from a first branch 14 through a first extension 16. In this case, an insertion bore 72 corresponding to the insertion passage 71 is provided in the first operation portion 19. The insertion bore 72 of the insertion passage 71 can be provided in the front end, side surface, or rear end of the main body of the first operation portion 19. The configuration is similar to that of the above-described first embodiment in other respects.

FIG. 20 is a diagram schematically showing a configuration according to a third embodiment of the present invention. In the present embodiment, an insertion bore 72 of observation section attaching/detaching mechanism (insertion passage) is provided at the proximal end portion of a body cavity insertion portion 12. Therefore, a first branch 14 is located in the proximal side to the insertion bore 72. In the present embodiment, as the first branch 14 is located in the proximal side to the insertion bore 72, observation unit attaching/detaching mechanism (observation section attaching/detaching mechanism) can be configured irrespective of a connection portion that connects the body cavity insertion portion 12 so that the body cavity insertion portion 12 can be separated from the operation portion side. The configuration is similar to that of the above-described first embodiment in other respects.

Figure 21:
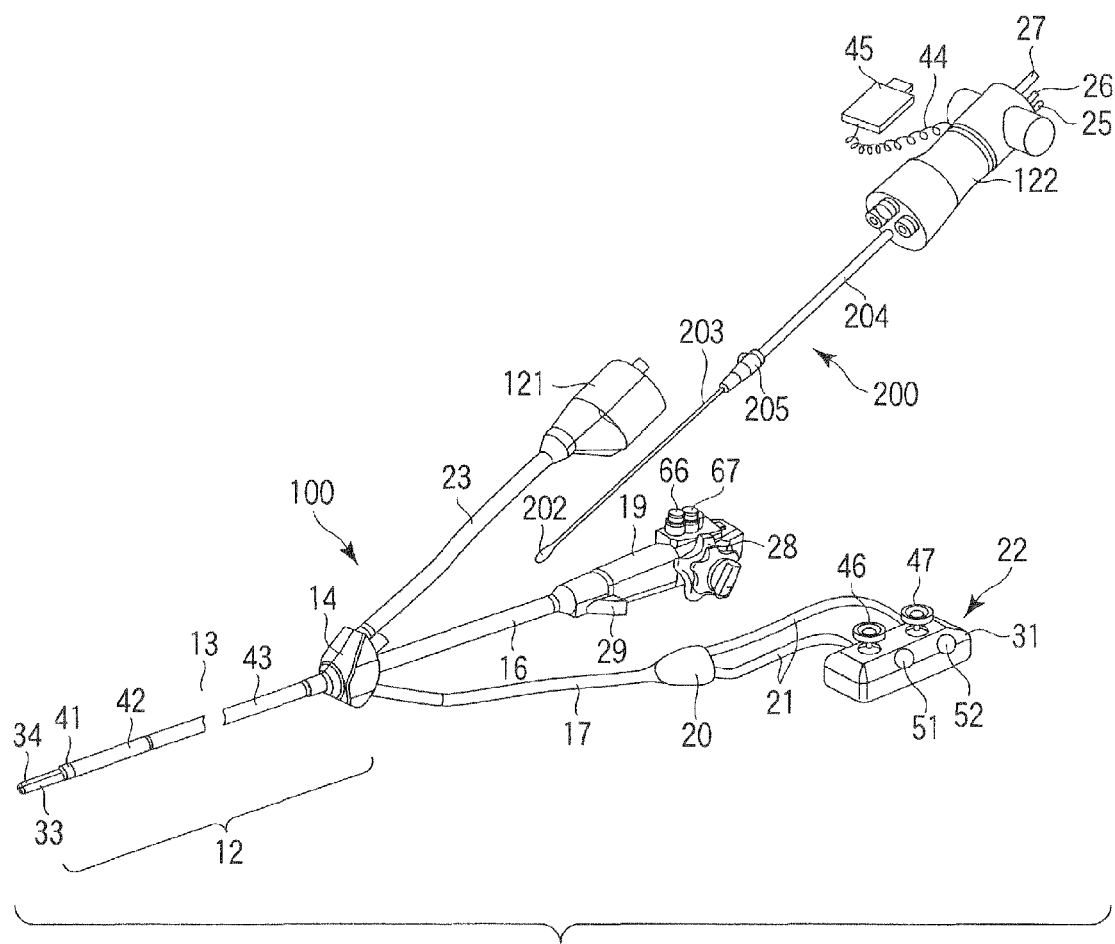
FIG. 21 is a perspective view schematically showing an entire treatment endoscope according to a fourth embodiment, of the present invention.

FIG. 21 is a diagram schematically showing a configuration according to a fourth embodiment of the present invention. Although the universal cord 23 is extended to the proximal side from the first operation portion 19 in the first embodiment as shown in FIG. 1, a universal cord 23 is extended to the proximal side from a first branch 14 in the present embodiment. That is, the universal cord 23 is separated from a first operation portion 19 in the first branch (universal cord branch) 14. A first link connector 121 is provided at the proximal end of the universal cord 23. The first link connector 121 is connectable to a second link connector 122 similar in configuration to the link connector 24 in the first embodiment (see FIG. 1).

Therefore, a link connector having a similar function to that of the link connector 24 in the first embodiment can be configured by connecting the first link connector 121 to the second link connector 122.

In the present embodiment, the universal cord 23 is extended to the proximal side not from the first operation portion 19 but from the first branch 14. Thus, the weight on the side of the first operation portion (main body operation portion) 19 can be reduced by the weight of the universal cord 23 and members connected to the universal cord 23. Accordingly, the first operation portion 19 can be easily operated without any load and restrictions imposed by the universal cord 23, thereby improving the operability of the first operation portion 19.

Figure 22:
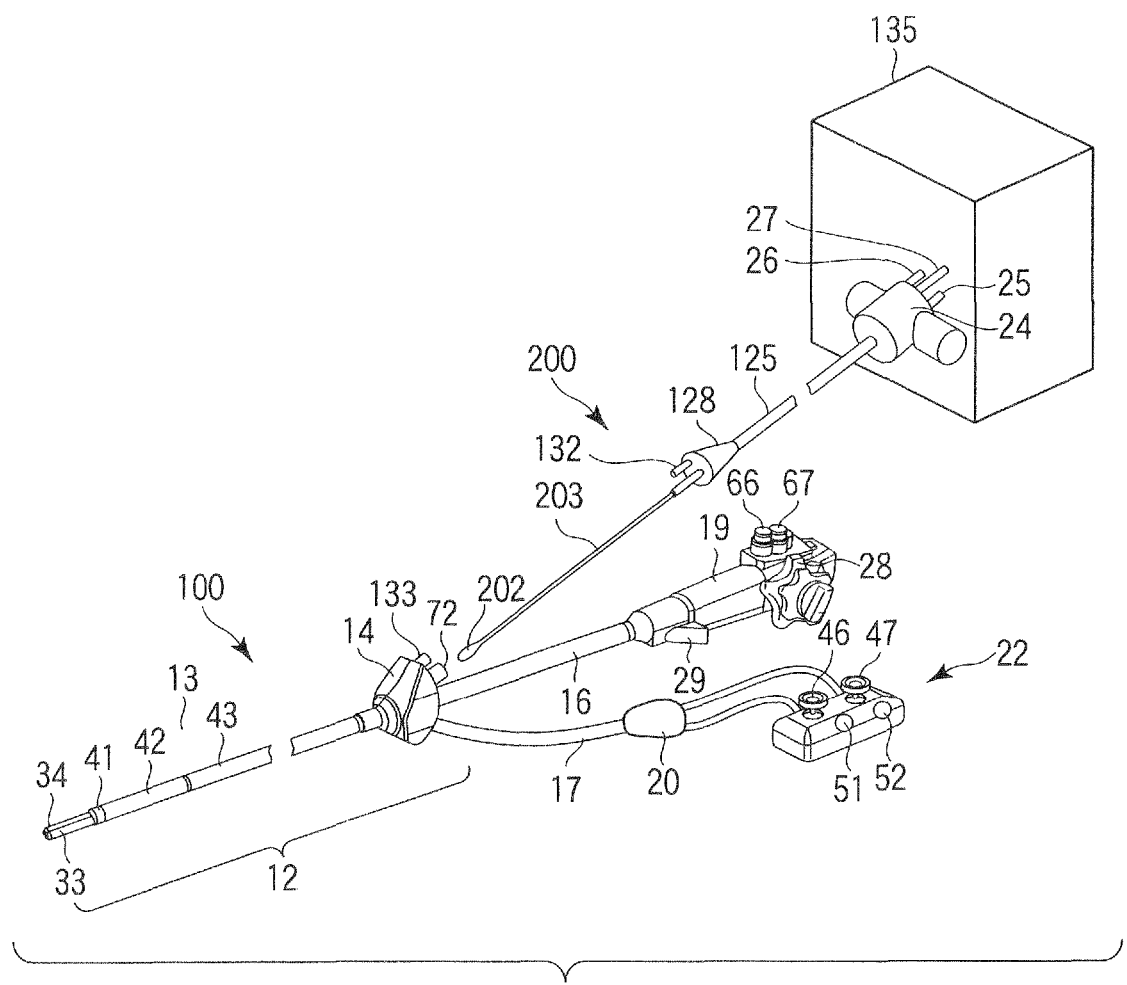
FIG. 22 is a perspective view schematically showing an entire treatment endoscope according to a fifth embodiment of the present invention.

FIG. 22 is a diagram schematically showing a configuration according to a fifth embodiment of the present invention. In the first embodiment (see FIG. 1), the universal cord 23 and the observation unit (observation section) 200 are separate from each other. However, in the present embodiment, a universal cord 23 is formed integrally with a cable unit 204 of the observation unit 200 to configure a universal cord (integral universal cord) 125. A first link connector 128 is provided between the insertion portion 203 of the observation unit 200 and the universal cord 125. The first link connector 128 is detachably connected to a first branch 14. The first link connector 128 is provided with a connection terminal 132 configured to connect, to the side of the insertion portion main body 13, internal objects such as tubes including an air supply tube, a water supply tube, and a suction tube, and a light guide that are connected to a treatment endoscope main body through the universal cord 125. The connection terminal 132 is detachably connected to a socket 133 provided in the first branch 14, so that the first link connector 128 is coupled to the side of the insertion portion main body 13. It should be noted that in the present embodiment, an air supply/water supply operation button, a suction operation button, and switches provided in an operation portion 19 may placed on a side of a console device 135.

In the present embodiment, the universal cord 23 is formed integrally with the cable unit 204 of the observation unit 200, thereby configuring the common universal cord 125. Thus, cords connected to the console device 135 from the operation portion can be combined into one, such that workability in, for example, the assembly of the members on the side of the operation portion is improved.

Figure 23A:
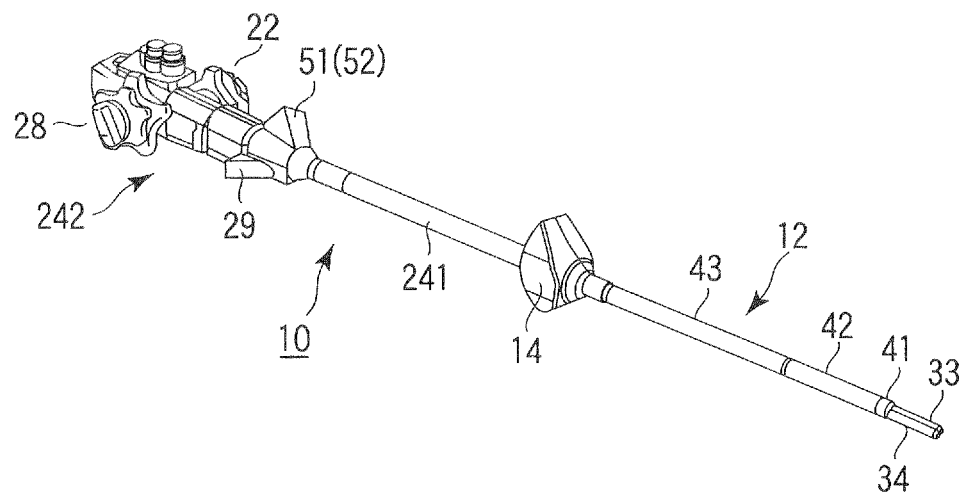
FIG. 23A is a perspective view schematically showing a treatment endoscope according to a sixth embodiment of the present invention.
Figure 23B:
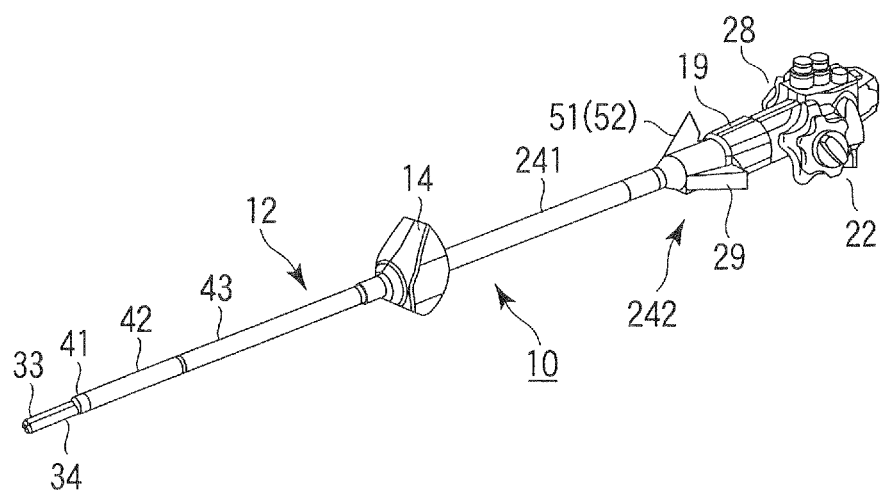
FIG. 23B is a perspective view schematically showing the treatment endoscope according to the sixth embodiment in a different direction from FIG. 23A.

FIG. 23A to FIG. 23C are diagrams showing a treatment endoscope according to a sixth embodiment. In the treatment endoscope according to the present embodiment, one flexible extension 241 is extended to the proximal side from the proximal end of a body cavity insertion portion 12. An operation portion 242 is provided at the proximal end of the extension 241. The operation portion 242 is operation mechanism that includes both the functions of the first operation portion (main body operation portion) 19 and the second operation portion (arm operation portion) 22 described above. As the first operation portion 19 and the second operation portion 22 are disposed at one operation position without being separate from each other, one operator can easily operate both the operation portions 19 and 22. The integral treatment endoscope in which the operation portions are collected at one place in the present embodiment is suitable to the case where the treatment endoscope 10 is used by one person without the aid of any assistant. The configuration is similar to those of the above-described embodiments in other respects.

Although a pair of treatment arms are provided in the embodiments described above, the body cavity insertion portion may be configured to be provided with three or more treatment arms.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A treatment endoscope comprising:
a body cavity insertion portion which includes a main body distal hard portion, and a main body curving portion provided at a proximal side of the main body distal hard portion;
at least one treatment arm which includes a curving mechanism and projects to a distal side from the main body distal hard portion of the body cavity insertion portion;
an observation section configured to image a field of view in a body cavity, the observation section including an imaging section provided within the main body distal hard portion of the body cavity insertion portion;
a main body operation portion configured to input a curving operation to the main body curving portion;
an arm operation portion configured to input a curving operation to the curving mechanism of the treatment arm;
a branch which is provided at a proximal side of the body cavity insertion portion;
a first extension which extends from the branch toward the main body operation portion;
a second extension which is separated from the first extension in the branch and which extends from the branch toward the arm operation portion, the arm operation portion and the second extension being coupled with the main body operation portion and the first extension so that a coupled collective body is formed by the main body operation portion, the first extension, the arm operation portion and the second extension;
an operation portion integral attaching/detaching mechanism which is provided in the branch and which is configured to removably and integrally attach the coupled collective body to the body cavity insertion portion;
a first internal object which is extended toward the proximal side from the body cavity insertion portion through the operation portion integral attaching/detaching mechanism and the first extension, and which is configured to be pushed or pulled by the curving operation input via the main body operation portion to actuate the main body curving portion;
a second internal object which is extended toward the proximal side from the treatment arm through the operation portion integral attaching/detaching mechanism and the second extension, and which is configured to be pushed or pulled by the curving operation input via the arm operation portion to actuate the curving mechanism of the arm; and
an observation section attaching/detaching mechanism configured to removably attach the observation section to the body cavity insertion portion,
wherein the operation portion integral attaching/detaching mechanism includes an internal object connection portion configured to separably connect an insertion portion side part and an operation portion side part in the first internal object and the second internal object.

2. The treatment endoscope according to claim 1, wherein the at least one treatment arm includes a treatment arm comprising a first curving mechanism configured to curve in four directions, and a second curving mechanism which is provided at a proximal side of the first curving mechanism and which is configured to curve in two directions.

3. The treatment endoscope according to claim 1, wherein the at least one treatment arm comprises at least two treatment arms which separately curve independently of each other.

4. The treatment endoscope according to claim 1, further comprising:
a main body operation portion attaching/detaching mechanism configured to detachably connect the main body operation portion to the first extension; and
an arm operation portion attaching/detaching mechanism configured to detachably connect the arm operation portion to the second extension.

5. The treatment endoscope according to claim 1, wherein the branch includes a universal cord branch configured to separate a universal cord from the first extension, the universal cord being a bundle of a tubular member of an air supply/water supply tube, a power supply cable, and a signal cable that constitute a third internal object different from the first internal object and the second internal object.

6. The treatment endoscope according to claim 5, wherein the observation section includes an imaging cable, and the treatment endoscope includes an integral universal cord in which the imaging cable and the universal cord are integrated.

7. The treatment endoscope according to claim 1, wherein first connection ends which are connection ends of the insertion portion side parts of the first internal object and the second internal objects, are arranged side by side in the internal object connection portion, and
wherein second connection ends which are connection ends of the operation portion side parts of the first internal object and the second internal object, are arranged side by side at positions corresponding to the first connection ends.

8. A treatment endoscope comprising:
a body cavity insertion portion which includes a main body distal hard portion, and a main body curving portion provided at a proximal side of the main body distal hard portion;
at least one treatment arm which includes a curving mechanism and projects to a distal side from the main body distal hard portion of the body cavity insertion portion;
an observation section configured to image a field of view in a body cavity, the observation section including an imaging section provided within the main body distal hard portion of the body cavity insertion portion;
a main body operation portion configured to input a curving operation to the main body curving portion;
an arm operation portion configured to input a curving operation to the curving mechanism of the treatment arm;
a branch which is provided at a proximal side of the body cavity insertion portion;
a first extension which extends from the branch toward the main body operation portion;
a second extension which is separated from the first extension in the branch and which extends from the branch toward the arm operation portion;
an operation portion integral attaching/detaching mechanism which is provided in the branch and which is configured to removably attach the first extension and the second extension integrally to the body cavity insertion portion;

a first internal object which is extended toward the proximal side from the body cavity insertion portion through the operation portion integral attaching/detaching mechanism and the first extension, and which is configured to be pushed or pulled by the curving operation input via the main body operation portion to actuate the main body curving portion;

a second internal object which is extended toward the proximal side from the treatment arm through the operation portion integral attaching/detaching mechanism and the second extension, and which is configured to be pushed or pulled by the curving operation input via the arm operation portion to actuate the curving mechanism of the arm; and an observation section attaching/detaching mechanism configured to removably attach the observation section to the body cavity insertion portion, wherein the operation portion integral attaching/detaching mechanism includes an internal object connection portion configured to separably connect an insertion portion side part and an operation portion side part in the first internal object and the second internal object, wherein first connection ends which are connection ends of the insertion portion side parts of the first internal object and the second internal objects, are arranged side by side in the internal object connection portion, and wherein second connection ends which are connection ends of the operation portion side parts of the first internal object and the second internal object, are arranged side by side at positions corresponding to the first connection ends.

* * * * *